(12) United States Patent
Cerruti et al.

(10) Patent No.: US 10,085,664 B2
(45) Date of Patent: Oct. 2, 2018

(54) ELECTROCARDIOGRAPH WITH CHEST ASSEMBLY, WATERPROOF HOUSING, RECORDING MODULE AND WIRELESS TRANSCEIVER

(71) Applicant: AB Medica Holding S.p.A., Milan (IT)

(72) Inventors: Aldo Cerruti, Milan (IT); Antonino Paris, Milan (IT); Stefano Marchetti, Milan (IT); Mauro Picciafuoco, Milan (IT)

(73) Assignee: AB Medica Holding S.p.A., Milan (IT)

( * ) Notice: Subject to any disclaimer, the term of this patent is extended or adjusted under 35 U.S.C. 154(b) by 163 days.

(21) Appl. No.: 15/111,076

(22) PCT Filed: Jan. 14, 2015

(86) PCT No.: PCT/IB2015/050277
§ 371 (c)(1),
(2) Date: Jul. 12, 2016

(87) PCT Pub. No.: WO2015/107465
PCT Pub. Date: Jul. 23, 2015

(65) Prior Publication Data
US 2016/0374583 A1    Dec. 29, 2016

(30) Foreign Application Priority Data
Jan. 14, 2014   (IT) .............................. MI2014A0035

(51) Int. Cl.
*A61B 5/00*      (2006.01)
*A61B 5/0432*   (2006.01)
(Continued)

(52) U.S. Cl.
CPC .......... *A61B 5/0432* (2013.01); *A61B 5/0006* (2013.01); *A61B 5/01* (2013.01);
(Continued)

(58) Field of Classification Search
CPC ....... A61B 5/0006; A61B 5/01; A61B 5/0404; A61B 5/04085; A61B 5/0432; A61B 5/11;
(Continued)

(56) References Cited

U.S. PATENT DOCUMENTS

| 6,603,995 B1* | 8/2003 | Carter | .................. A61B 5/0404 600/509 |
| 2005/0119584 A1* | 6/2005 | Carter | .................. A61B 5/0404 600/528 |

(Continued)

FOREIGN PATENT DOCUMENTS

| EP | 1467651 B1 | 10/2008 |
| GB | 2368127 A  | 4/2002  |

(Continued)

OTHER PUBLICATIONS

International Search Report and Written Opinion for International Application No. PCT/IB2015/050277,( dated May 11, 2015) (11 Pages).

*Primary Examiner* — Michael Carey
(74) *Attorney, Agent, or Firm* — Lucas & Mercanti LLP

(57) ABSTRACT

A electrocardiograph having a chest assembly intended to be applied to the chest region of a patient and an electronic unit is provided, with a recording module and with a wireless transceiver module. The chest assembly has a plurality of electrodes configured to be connected to the patient's body for the recording of an electrocardiogram and respective electrical wires connecting each electrode to the electronic unit. The chest assembly further includes a housing to which the electrical wires are respectively fixed. The electronic unit has a Hall-effect magnetic sensor configured to selectively allow it to mark, to start, stop, record and send an electrocardiogram to a telecommunications network. The electrocardiograph further includes a magnet mounted on a sup- (Continued)

porting member configured to be worn by a patient to activate the Hall-effect magnetic sensor.

11 Claims, 3 Drawing Sheets

(51) Int. Cl.
    *A61B 5/0404*     (2006.01)
    *A61B 5/0408*     (2006.01)
    *A61B 5/01*     (2006.01)
    *A61B 5/11*     (2006.01)

(52) U.S. Cl.
    CPC ........ *A61B 5/0404* (2013.01); *A61B 5/04085* (2013.01); *A61B 5/11* (2013.01); *A61B 5/6833* (2013.01); *A61B 5/74* (2013.01); *A61B 5/7405* (2013.01); *A61B 5/7455* (2013.01); *A61B 5/7465* (2013.01); *A61B 5/681* (2013.01); *A61B 2560/0214* (2013.01); *A61B 2560/0219* (2013.01); *A61B 2560/0223* (2013.01); *A61B 2560/0252* (2013.01); *A61B 2560/0443* (2013.01); *A61B 2562/222* (2013.01); *A61B 2562/225* (2013.01)

(58) Field of Classification Search
    CPC ......... A61B 5/651; A61B 5/3833; A61B 5/74; A61B 5/7405; A61B 5/7455; A61B 5/7465; A61B 2560/0214; A61B 2560/0219; A61B 2560/0223; A61B 2560/0252; A61B 2560/0443; A61B 2562/222; A61B 2562/225
    USPC .................................................. 600/300, 301
    See application file for complete search history.

(56) References Cited

U.S. PATENT DOCUMENTS

| 2008/0177168 A1 | 7/2008 | Callahan et al. |
| 2009/0216147 A1 | 8/2009 | Van Eijkern |
| 2010/0042008 A1* | 2/2010 | Amitai ................ A61B 5/0404 600/509 |
| 2012/0003933 A1* | 1/2012 | Baker ................ G06F 19/3412 455/41.2 |
| 2013/0204100 A1* | 8/2013 | Acquista ............ A61B 5/0006 600/301 |

FOREIGN PATENT DOCUMENTS

| GB | 2472769 A * | 2/2011 | ............. H02J 7/025 |
| WO | 2012160550 A1 | 11/2012 | |
| WO | WO 2012160550 A1 * | 11/2012 | ........... A61B 5/0404 |
| WO | 2013190471 A1 | 12/2013 | |

\* cited by examiner

ELECTROCARDIOGRAPH WITH CHEST ASSEMBLY, WATERPROOF HOUSING, RECORDING MODULE AND WIRELESS TRANSCEIVER

CROSS-REFERENCE TO RELATED APPLICATIONS

This application is a 371 of PCT/IB2015/050277, filed Jan. 14, 2015, which claims the benefit of Italian Patent Application No. MI2014A000035 filed Jan. 14, 2014.

FIELD OF THE INVENTION

The present invention generally relates to systems for monitoring cardiac activity and in particular to an electrocardiograph.

BACKGROUND OF THE INVENTION

An electrocardiogram, also known by the acronym ECG, is the graphic representation of the electrical activity of the heart during its operation, which is recorded by way of electrodes applied on the surface of the body of a patient in the thoracic region.

Measuring heart electrical activity is based on a physiological principle. The onset of electrical impulses in the myocardium in fact causes potential differences varying over space and time that can be recorded through a plurality of electrodes contacting the body of a patient in predetermined locations known as "leads". The conductive surface of the electrodes is covered with a suitable ionic gel decreasing the contact impedance between skin and electrode, while contact is favored by way of suction pads, bandages or the like applied to the individual electrodes, or by way of suitable chest belts on which a number of electrodes are mounted at predetermined positions. The registration of the potential differences by the electrodes is possible thanks to the conductivity of the interstitial fluids of the human body.

An electrocardiogram is a very effective tool for monitoring the electrical activity of the heart and for detecting mechanical or bioelectrical pathologies.

The electrodes of an electrocardiograph are connected to an electronic recording unit through respective electrical wires. The recording unit is for example a remote unit to which the electrical wires are connected. Therefore, when recording an electrocardiogram a patient is connected to the electronic recording unit through the electrical wires. This is rather uncomfortable, because the wires partially rest on the patient's body and must be carefully arranged by a doctor so that they do not interfere with each other.

In order to improve and simplify the connection mode between each electrode and the electrical recording unit there have been developed electrocardiographs including a connection unit that may be worn by a patient. Connection units are provided with a plurality of input connectors to which the electrodes may be connected, as well as with an output connector configured to allow connection of a single wire for the transmission of the data acquired through the electrodes to a remote electronic recording unit.

The publication US 2008/0177168 A1 e.g. discloses a device for recording an electrocardiogram comprising a plurality of electrodes that may be individually connected through respective electrical wires to a connection unit or "hub" that is arranged on the body of a patient. The electrode wires are extensible so as to allow positioning of the electrodes according to a desired lead arrangement. In addition to the connectors for the electrode wires, the electronic connection unit comprises a further connector which allows connection of a wire for the transmission of the data acquired through the electrodes to a remote recording unit.

Also known are wireless electrocardiographs wherein the electrodes are connected to a portable electronic unit that may be worn by a patient. The electronic unit is provided with a transmitter that allows data transmission to a fixed unit or base connectable to a monitoring equipment of a traditional type. The European patent EP 1467651 B1 describes an example of a device of this type.

The publication GB 2368127 A discloses another example of a wireless electrocardiograph that comprises an electronic unit and a chest assembly provided with a housing for the electronic unit and with a plurality of electrical wires with respective electrodes. The electronic unit is detachable from the chest assembly.

Also known are the so-called "Holter" electrocardiographs, from the name of their inventor, designed to monitor the electrical activity of the heart over long periods, for example 24 hours or a few days, during which a patient may lead a normal life. Holter devices comprise a plurality of electrodes that are connected to the body of a patient according to lead patterns that are similar to the lead patterns used for the recording of a traditional electrocardiogram, as well as a portable electronic unit configured to be worn by the patient. The portable electronic unit includes an electronic unit-configured for recording, storing and sending to a remote processing unit the data acquired through the electrodes.

Holter type electrocardiographs are generally more complex than those used for ambulatory recording of electrocardiograms, because they have to perform monitoring over much longer periods during which a patient may lead his life according to his normal habits. Consequently, electrical energy consumption problems must be carefully considered in the design of these devices.

Energy consumption is a very important problem even in non-Holter electrocardiographs, which carry out a real-time monitoring of a patient and are configured for the transmission of data in wireless mode, which results in a high consumption of energy.

The interaction of patients with known electrocardiographs, as well as data transmission and energy consumption may be improved. The technical problem underlying the present invention is therefore to provide an electrocardiograph which allows to overcome the drawbacks mentioned above with reference to the prior art.

This problem is solved by a device according to claim 1. Preferred features of the present invention are object of the dependent claims.

SUMMARY OF THE INVENTION

An idea of solution underlying the present invention is to provide an electrocardiograph comprising a chest assembly provided with a plurality of wires and respective electrodes connected to the body of a patient for the recording of an electrocardiogram, as well as an electronic unit mounted on the chest assembly and electrically connected to electrodes through a connector. The electronic unit is provided with a recording module and a wireless transceiver and includes a Hall-effect magnetic sensor configured to selectively start and stop recording of an ECG on a memory module, as well as to send ECG registrations to a telecommunications network through an external gateway, and to mark an electrocardiogram e.g. in case of a sudden illness. The same sensor may be used to send emergency calls, for example to a medical doctor or to a medical care center. The electrocardiograph further includes a magnet for the activation of the Hall-effect magnetic sensor, said magnet being mounted on a supporting member that may be worn by a patient during a monitoring period.

Thanks to these features, it is possible to provide an electrocardiograph allowing interaction between patient and medical doctor or medical care center.

An advantage offered by the invention is that the ability to selectively send, i.e. upon input of the patient, ECG records to a telecommunications network in a wireless mode allows to optimize energy consumption of the batteries.

Thanks to this feature it is possible to maintain the electronic unit in a so-called "deep sleep" condition when the medical protocol followed by a patient does not provide for activation of the unit. In this operating condition the electric energy consumption is in the order of picoampere, which allows to maximize battery life.

The electronic unit is preferably powered by a rechargeable battery that may be recharged by placing the unit in a special electronic base connected to the mains via a common wire. Still more preferably, the electronic unit is configured for wireless charging in resonant mode, thus allowing a user to continue to wear the electrocardiograph during the charging period.

According to an embodiment of the invention, the electronic unit of the electrocardiograph is configured to be removably fitted in the housing of the chest assembly and includes a contact interface configured for electrical connection with the terminals of the electrode wires. The chest assembly is of disposable type and once recording of an electrocardiogram is finished, the electronic unit is detached from the housing and the chest assembly is completely replaced to record a new electrocardiogram.

This configuration has the advantage of providing cardiologists and patients with a modular electrocardiograph wherein not only the electrodes, but also the wires and the housing to which they are connected may be removed and replaced after each use, thus ensuring a high level of sterility of the parts intended to come into contact with the body of a patient.

Another advantage offered by the invention is that the electrocardiograph may be used both for real-time recording of an ECG, for example in a medical center, and as a Holter device for long term monitoring.

BRIEF DESCRIPTION OF THE DRAWINGS

Further advantages and features of the electrocardiograph according to the present invention will become clear to those skilled in the art from the following detailed and non-limiting description of an embodiment thereof with reference to the accompanying drawings wherein.

DETAILED DESCRIPTION OF THE INVENTION

Figure 1:
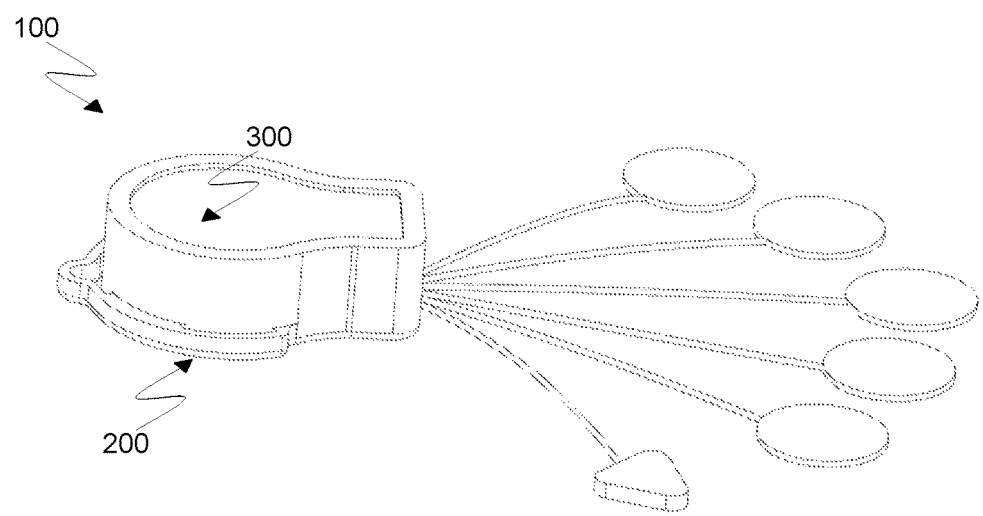
FIG. 1 is a perspective view showing an electrocardiograph according to the invention.

Referring to the drawings an electrocardiograph according to the invention is generally indicated by reference numeral 100 and includes a chest assembly 200 and an electronic unit 300.

The chest assembly 200 in turn comprises a plurality of electrodes that may be connected to the body of a patient so as to allow recording of an electrocardiogram, as well as respective connection wires to the electronic unit 300.

In the illustrated embodiment, the chest assembly 200 e.g. comprises five electrodes indicated by reference numbers 201, 202, 203, 204, 205 which allow to record electrocardiograms according to the known seven leads pattern. The wires of the electrodes 201, 202, 203, 204, 205 are respectively indicated by reference numbers 211, 212, 213, 214, 215.

It will be understood that such a number of electrodes and wires is purely indicative and that the chest assembly 200 may include additional electrodes and wires in order to create acquisition patterns with more than seven leads.

Figure 3:
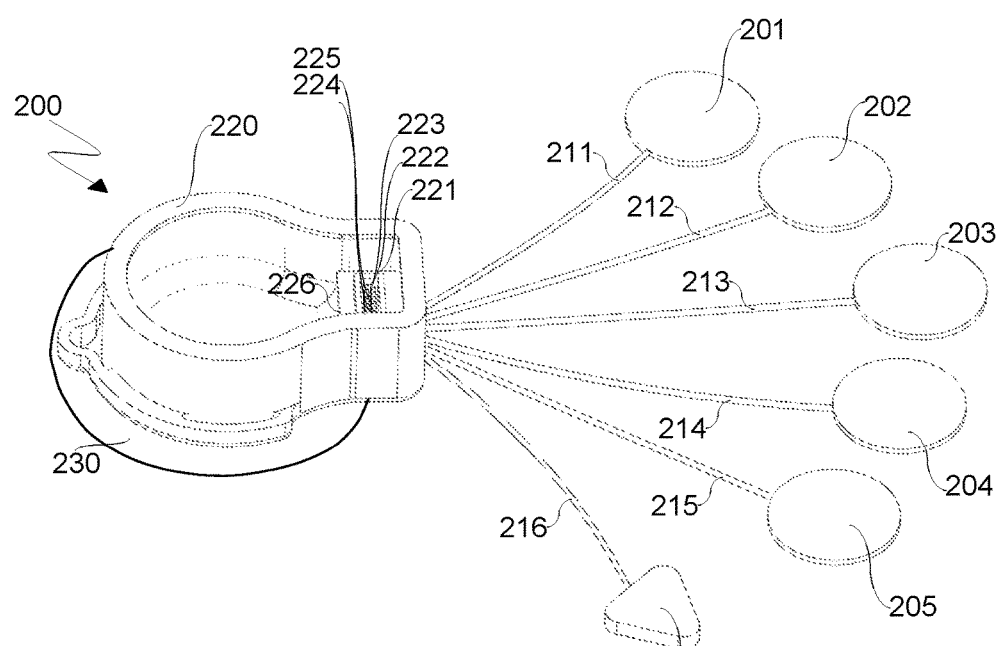
FIG. 3 is a perspective view showing a chest assembly of the electrocardiograph of FIG. 1.

With reference to FIG. 3, the chest assembly 200 also comprises a housing 220 to which the wires 211, 212, 213, 214, 215 of the electrodes 201, 202, 203, 204, 205 are respectively fixed. The electrical terminals 221, 222, 223, 224, 225 of the wires 211, 212, 213, 214, 215 are restrained to the housing 220.

In the illustrated embodiment, for example, the housing 220 has a substantially hollow cylindrical shape and the electronic unit 300 has a cylindrical shape and size matching those of the cylindrical housing 220.

The housing 220 includes a radially protruding portion that defines a cavity housing the electrical terminals 221, 222, 223, 224, 225. The electrical terminals 221, 222, 223, 224, 225 may be configured as connection pins arranged according to a predefined pattern, for example next to each other, and are preferably arranged in a seat 226 configured to receive a connector of the electronic unit 300. As shown in FIG. 3, the seat 226 is formed in the radially protruding portion of the housing 220.

Figure 4:
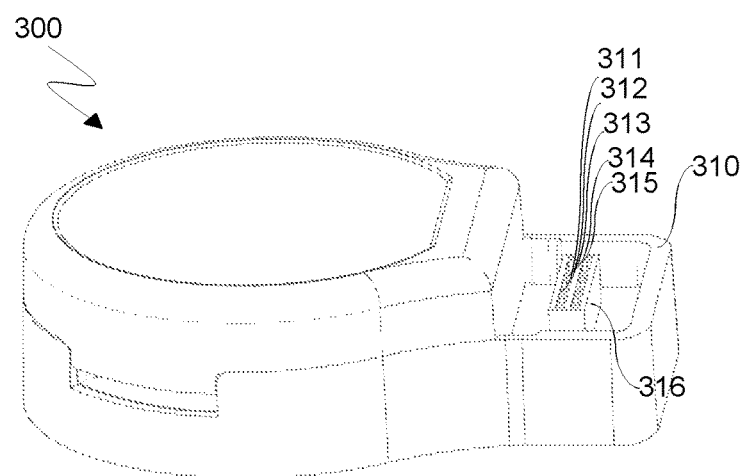
FIG. 4 is a perspective view showing an electronic unit of the electrocardiograph of FIG. 1.

Now referring to FIG. 4, the electronic unit 300 correspondingly comprises a contact interface 310 configured for connection with the electrical terminals 221, 222, 223, 224, 225 of the electrode wires restrained to the housing 220. To this aim, the contact interface 310 radially protrudes from the electronic unit 300 and includes a plurality of electrical terminals the number of which corresponds to the number of the electrical terminals of the electrodes.

Still with reference to FIG. 4, in the illustrated embodiment the electrical terminals are e.g. five and are indicated by reference numbers 311, 312, 313, 314, 315. The electrical terminals are arranged according to a predefined pattern corresponding to the pattern of the electrical terminals of the electrode wires, for example next to one another, and are restrained to a connector 316 whose a shape matches the shape of the seat 226, so that by fitting the electronic unit 300 into the housing 220 of the chest assembly 200 the electrical terminals 311, 312, 313, 314, 315 of the electronic unit are respectively coupled with the electrical terminals 221, 222, 223, 224, 225 of the wires of the electrodes 201, 202, 203, 204, 205.

It will be understood that the above described arrangement of the electrical terminals of the wires of the chest assembly 200 and of the electrical terminals of the electronic unit 300 is only a non-limiting example of the invention and that the terminals might be arranged in other equivalent ways.

The electrocardiograph 100 according to the invention is designed as a wireless device. To this aim, the electronic unit 300 comprises a recording module (not shown) for storing the signals acquired through the electrodes, thus being able to operate both as a traditional electrocardiograph and as a Holter-type device for monitoring the cardiac activity of a patient over prolonged periods of time.

The recording module of the electronic unit 300 may advantageously be provided with a removable mass storage device, such as a "Secure Digital" card also known by the acronym SD, which facilitates data transfer and sharing. The transfer of data from the recording module of the electronic unit may alternatively be made by way of an infrared port, or a BLUETOOTH® (e.g., wireless) transmitter and the like.

The electronic unit 300 may also be advantageously provided with a wireless transceiver module, such as a BLUETOOTH® or equivalent wireless module, in order to allow exchange of data with an external electronic unit, such as a computer, a smartphone, or, more generally, an electronic device. This configuration allows to display, analyze and possibly send data concerning monitoring of the cardiac activity of a patient through a suitable software application, but also to receive configuration data from remote, as well as updated versions of the software managing operation of the electronic unit 300 and the like.

The electronic unit 300 further comprises a Hall effect magnetic sensor (not shown) configured to allow to selectively start and stop registration of an ECG, as well as to send ECG records to a telecommunications network through an external gateway.

The magnetic sensor may also be advantageously exploited to allow a patient to mark a particular ECG e.g. upon a sudden illness so as to send an alarm. To this aim, the electronic unit may advantageously be programmed to send marked ECG data together with data relating to a preceding time span having a predetermined duration, for example a few seconds.

The Hall effect magnetic sensor is activated directly by a patient by means of a magnet 400 of the electrocardiograph 100 mounted on a suitable supporting member, for example a bracelet 410, that may be worn by a patient during a monitoring period, and that must be simply placed near the electrocardiograph 100.

Figure 5:
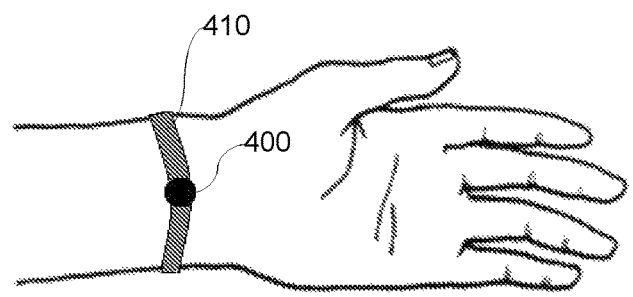
FIG. 5 is a perspective view showing a magnet for the activation of a magnetic sensor of the electronic unit of the electrocardiograph according to the invention, the magnet being arranged on a bracelet to be worn by a patient.

FIG. 5 shows a forearm of a patient on which a bracelet 410 with the magnet 400 may be seen.

The patient may thus interact with and directly manage the electrocardiograph according to the invention so as to carry out extemporaneous activities and manage emergencies, which goes beyond normal operation of a Holter device that generally operates in a fully automatic manner. This particular configuration of the electrocardiograph of the invention meets the increasing need in the field to make remote monitoring of a patient more and more simple and flexible and, more generally, to improve adherence of a patient to a medical protocol.

The electronic unit 300 is powered by a battery (not shown) arranged in a special compartment (not shown). For ease of use, this battery is preferably rechargeable type.

According to a preferred embodiment of the invention, the electronic unit 300 is configured for wireless charging in a resonant mode. As it is known, this type of charging involves the use of a transmitter unit and a receiver unit that are respectively connected to a power supply and to a device to be powered, these units consisting of windings configured to have the same resonance frequency.

The electronics unit 300 may thus advantageously comprise a winding connected to an electric circuit for charging the rechargeable battery for its wireless charging in a resonant mode.

The resonant charging may for example be carried out by way of an inductive coupler placed in contact with the portion of the device to be recharged wherein the resonant winding is housed.

Wireless resonant charging of the battery of the electronic unit 300 may be advantageously carried out by way of a recharging apparatus as that described in the International Publication WO 2013/190471 A1 in the applicant's name. Such apparatus comprises a modular compartment adapted to define a closed environment wherein a patient may be received; the apparatus further comprises at least one pair of windings associated with the compartment walls and arranged perpendicular to each other. The windings are configured to radiate an electromagnetic field towards the inside of the closed environment when supplied with alternating current. A power and driving system of the windings of the modular compartment generates a rotating magnetic field inside the closed environment that may power the resonant winding of the electronic unit 300 regardless of its position in the space, i.e. whatever the position of the patient inside the closed environment is. The closed environment wherein the electronic unit 300 of the electrocardiograph can be recharged may be either a hospital room 100 or a domestic environment.

Alternatively, the rechargeable electronic unit 300 may be recharged by using a suitable base connected to a power supply via a suitable electric wire.

The electronic unit 300 is configured to maintain a "deep sleep" operation mode when not activated by the Hall-effect magnetic sensor. This allows to maximize the battery life, because in the "deep sleep" mode energy consumption is in the order of picoampere.

According to a further aspect of the invention, the electronic unit 300 may advantageously comprise a radio frequency identification system known by the acronym RFID (Radio Frequency IDentification), for automatic identification of the patient subjected to the monitoring and/or to a charging process. This configuration is particularly advantageous when considering use and charging in a resonant mode of the electrocardiograph 100 in a hospital, and even more particularly in a hospital room configured as a closed environment provided with a recharging apparatus as disclosed in the international publication WO 2013/190 471 A1. RFID identification may e.g. be used as a means to allow selectively restrict access of patients to a charging room, to automatically activate a wireless charging function in a resonant mode, as well as any device for receiving data acquired through the electrodes of the chest assembly 200 and transmitted by the electronic unit 300.

The electronic unit 300 of the electrocardiograph according to the invention may also advantageously comprise further electronic devices such as one or more motion sensors (not shown) and a temperature sensor 206, connected to the electronic unit 300 via a respective wire 216 suitable to allow acquisition and recording of additional data that may contribute to the definition of the clinical condition of a patient being monitored.

The electronics module 300 may also be advantageously equipped with a loudspeaker and a microphone allowing a professional to instruct patients about specific measures concerning the activities they must carry out.

Any assistance request may be sent by a patient using the Hall-effect magnetic sensor the electronic unit 300 is provided with.

The loudspeaker may also be used to send acoustic signals to the patient, for example a sound signal upon start of the recording of an electrocardiogram, a reminder signal when the patient must start monitoring by activating the electronic unit 300, an alarm signal when the battery is low, and the like. The electronic unit 300 may also advantageously comprise a vibrator associated with the loudspeaker, which allows to combine the audio signals with mechanical vibrations thanks to the contact with the chest of the user through the chest assembly 200, thus making signals concerning the operation condition of the electrocardiograph 100 more and more clear for patients, especially in noisy environments.

In light of the above, it will be understood that the electrocardiograph 100 according to the invention is configured as a portable device to be worn by a patient. To this aim it is e.g. possible to foresee the use of a necklace that may be worn around a patient's neck and to which the chest assembly 200 or the electronic unit 300 may be hung.

According to an embodiment of the present invention, the electronic unit 300 is configured to be removably fitted into the housing 220 of the chest assembly 200 and the latter is of a disposable type.

Figure 2:
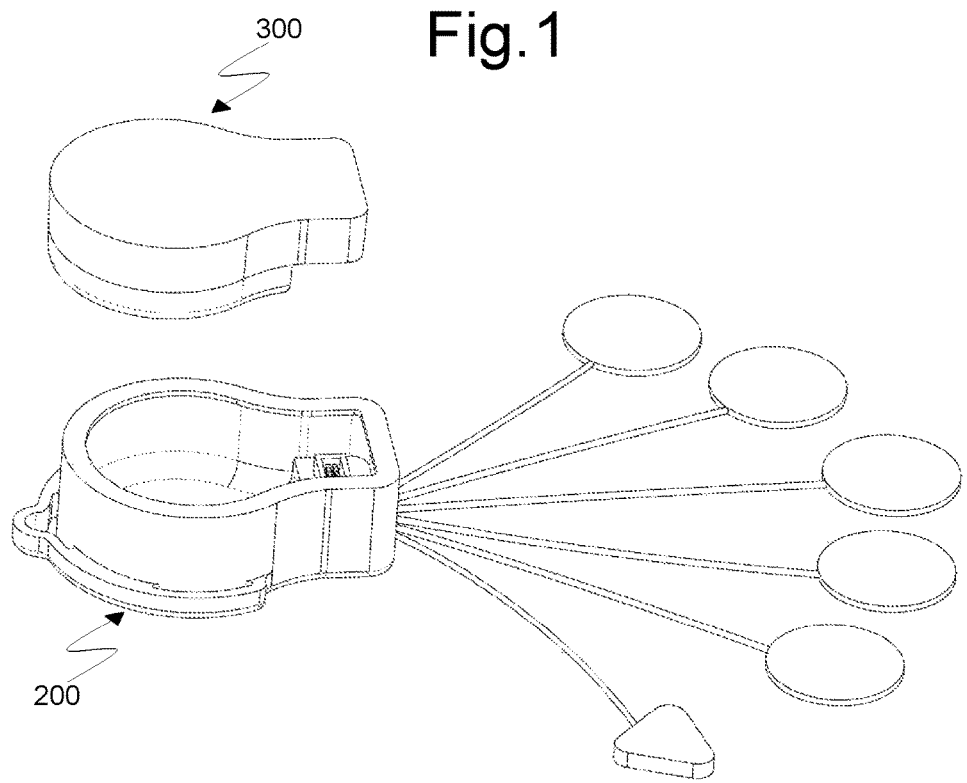
FIG. 2 is an exploded perspective view of the electrocardiograph of FIG. 1.

The removable connection between the electronic unit 300 and the housing 220 may e.g. be a snap fit connection, as shown in FIGS. 2, 3 and 4, or an interlocking one and any other equivalent connection known to those skilled in the art.

The connection between the housing 220 and the electronic unit 300 is preferably waterproof and to this purpose the electrocardiograph 100 may further include a peripheral gasket (not shown) arranged on the edge of the housing 220 of the chest assembly 200 or on the edge of the electronic unit 300. This configuration allows to use the electrocardiograph according to the invention also in presence of water, for example when the patient is washing himself, and allows to preserve the electrical parts from moisture and sweat.

For the same reasons, the electronic unit 300 may advantageously comprise a watertight casing. The casing is preferably free of buttons so as to ensure maximum tightness conditions, but any buttons may be arranged on the side of the electronic unit 300 facing the inside of the housing 220, thus being protected from the contact with water or other fluids by the watertight coupling between the housing 220 and the electrical unit 300 described above.

Once the recording of an electrocardiogram is finished, the electronic unit 300 may be disconnected from the housing 220 and the disposable chest assembly 200 may be entirely replaced so as to record a new electrocardiogram. In this way all the parts of the system that come into contact with the patient's skin and that, consequently, are subject to fouling problems are replaced with respective new parts of the electrocardiograph, thus ensuring a high level of sterility and hygiene to the patients.

The electronic unit 300 is therefore the only component of the electrocardiograph which is reused, because, thanks to the provision of the housing 220 of the chest assembly 200, it is the only part that does not contact the patient's body.

Figure 6:
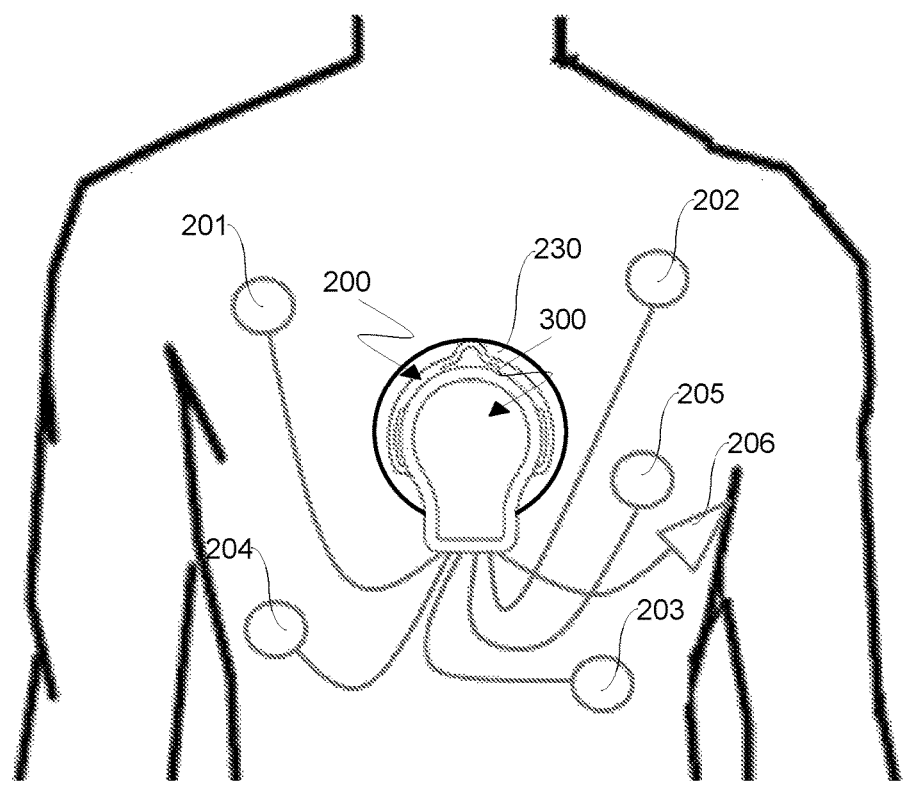
FIG. 6 is a front view schematically showing the electrocardiograph of FIG. 1 applied to the chest of a patient.

According to a further aspect of the invention and still with reference to FIGS. 3 and 6, in order to ease positioning of the electrocardiograph 100 on the body of a patient, the chest assembly 200 may advantageously comprise an adhesive member 230, such e.g. as a patch. This configuration of the electrocardiograph 100 allows an operator to initially fix the position of the housing 220 of the chest assembly 200 and then to arrange the electrodes with respect to the housing according to a predefined lead pattern. FIG. 6 schematically shows the electrocardiograph applied to the chest of a patient.

This configuration of the electrocardiograph 100 is extremely advantageous, because it allows to achieve an extremely stable position of the device on the patient's body, while avoiding to resort to laces which may be uncomfortable for the patient, especially in the case of long-term monitoring.

Furthermore, provision of an adhesive member associated with the chest assembly 200 is synergistic with the concept of modularity of the electrocardiograph, because the fixing means are associated with the chest assembly 200 and are disposable like the latter, thus ensuring a high sterility level of the interchangeable components of the electrocardiograph 100.

The present invention has hereto been disclosed with reference to preferred embodiments thereof. It is understood that there may be other embodiments relating to the same inventive idea as defined by the scope of protection of the claims set forth below.

The invention claimed is:

1. A electrocardiograph having a chest assembly intended to be applied to the body of a patient in the chest region and an electronic unit provided with a recording module and with a wireless transceiver module,
   wherein said chest assembly further comprises a plurality of electrodes configured to be connected to the body of a patient for the recording of an electrocardiogram and respective electrical wires connecting each electrode to said electronic unit, the chest assembly further comprising a housing to which said electrical wires are respectively fixed, and first electrical terminals of the wires being restrained to said housing,
   wherein said housing is provided with a contact interface configured to be electrically connected to the first electrical terminals, the contact interface comprising a plurality of second electrical terminals protruding outwards said housing and arranged according to a pattern corresponding to the pattern of first electrical terminals of the wires, the number of the second electrical terminals corresponding to the number of the first electrical terminals;
   wherein the electronic unit is enclosed in a watertight casing, is configured to be removably fitted in the housing and comprises a Hall-effect magnetic sensor configured to selectively allow, when activated by a magnet, the electronic unit to mark an electrocardiogram, to start and stop recording of an electrocardiogram and/or to send a record of an electrocardiogram to a telecommunications network, and
   wherein the electrocardiograph further comprises a magnet, separated from said housing, for the activation of said Hall-effect magnetic sensor when placed from the outside in proximity to said housing, said magnet being mounted on a supporting member configured to be worn by a patient during a monitoring period.

2. A electrocardiograph according to claim 1, wherein the housing has a substantially cylindrical hollow shape and comprises a radially protruding portion housing the first electrical terminals of the wires,
   wherein the first electrical terminals being configured as connection pins arranged according to a predetermined pattern in a seat formed in said radially protruding portion of the housing, and wherein the second electrical terminals housed in the contact interface are restrained to a connector the shape of which matches the shape of said seat.

3. A electrocardiograph according to claim 1, further comprising a peripheral sealing member arranged on the edge of at least one between the housing and the electronic unit.

4. A electrocardiograph according to claim 1, wherein the electronic unit comprises a battery of a rechargeable type.

5. A electrocardiograph according to claim 4, wherein the electronic unit comprises a circuit for charging the rechargeable battery, said circuit being provided with a winding configured for wireless power supply according to a resonant mode.

6. A electrocardiograph according to claim 1, wherein the electronic unit further comprises a radio frequency identification system (RFID) configured for automatic identification of a patient carrying the electrocardiograph.

7. A electrocardiograph according to claim 1, wherein the electronic unit further comprises a motion sensor and a temperature sensor.

8. A electrocardiograph according to claim 1, wherein the electronic unit also includes a loudspeaker and a microphone.

9. A electrocardiograph according to claim 8, wherein the electronic unit further comprises a vibrator associated with said loudspeaker.

10. A electrocardiograph according to claim 1, wherein the electronic unit has a substantially planar base providing a continuous, external surface upon insertion into the housing.

11. A electrocardiograph according to claim 10, wherein the substantially planar base is free of buttons to facilitate water tightness between the housing and the electronic unit inserted therein.

* * * * *